US00PP14495P29

(12) United States Plant Patent

Anderson et al.

(10) Patent No.: US PP14,495 P2

(45) Date of Patent: *Jan. 27, 2004

(54) CHRYSANTHEMUM PLANT NAMED MN98-89-7

(50) Latin Name: *Dendranthema×hybrida*
Varietal Denomination: MN98-89-7

(75) Inventors: Neil Anderson, St. Paul, MN (US); Peter Ascher, Bowler, WI (US); Esther Gesick, Maple Grove, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/999,733

(22) Filed: Oct. 30, 2001

(51) Int. Cl.[7] ..... A01H 5/00

(52) U.S. Cl. ..... Plt./286

(58) Field of Search ..... Plt./297, 286

(56) References Cited

U.S. PATENT DOCUMENTS

| | | | |
|---|---|---|---|
| PP7,513 | P | 4/1991 | VandenBerg |
| PP7,754 | P | 12/1991 | VandenBerg |
| PP9,445 | P | 1/1996 | VandenBerg |
| PP10,848 | P | 4/1999 | VandenBerg |
| PP10,909 | P | 5/1999 | Wain |
| PP10,943 | P | 6/1999 | Fuess |
| PP11,009 | P | 7/1999 | Davino, Jr. |
| PP11,032 | P | 8/1999 | Glicenstein |

OTHER PUBLICATIONS http://www.extension.umn.edu/distribution/horticulture/DG7352.html, "Maxi–Mums", 1997, pp. 1–2.*

Peter Ascher, et al., "Maxi–Mums A Horticulture Breakthrough!" Minnesota Report 242–1997 University of Minnesota, Distribution Center Publication MR–67280B Minnesota Agricultural Experiment Station, University of Minnesota (1997).

R.B. Clark, History of Culture of Hardy Chrysanthemums, National Chrysanthemum Society 18(3):144 (1962).

W.W. Garner, et al., Flowering and Fruiting of Plants as Controlled by the Length of Day, 1920, p. 377–400, Yearbook of the Department of Agriculture, 1920 USA.

Peter Ascher, et al., Breeding and New Cultivars, Academic Perspective, Tips on Growing and Marketing Garden Mums, Ohio Florists Association 1996.

Bradford Bearce et al., Chrysanthemums A Manual of the Culture, Diseases, Insects and Economics of Chrysanthemums, Jun. 1964, pp. 6–19, Prepared for The New York State Extension Service Chrysanthemum School with the Cooperation of the New York State Flower Growers Association, Inc.

Neil O. Anderson, et al., Rapid Generation Cycling of Chrysanthemum Using Laboratory Seed Developmenta nd Embryo Rescue Techniques, Journal of the American Society of Horticultural Science, Mar. 1990, pp. 329–336, vol. 115(2), Alexandria, Virginia 22314.

Leon Glicenstein, Breeding and New Cultivars, Commercial Perspective, Tips on Growing and Marketing Garden Mums, Ohio Florist's Association 1996.

M.A. Nazeer, et al., Cytogenetical Evolution of Garden Chrysanthemum, Current Science, Jun. 20, 1982, vol. 51, No. 12.

Edward Higgins, Containers and Marketing, Tips on Growing and Marketing Garden Mums, Ohio Florists Association 1996.

Naomasa Himotomai, Bastardierungsversuche bei Chrysanthemum I., Journal of Science of Hiroshima University, Series B, Div.2, vol. 1, Art. 3, 1931.

Naomasa Shimotomai, Basterdierungsversuche bei Chrysanthemum II. Eentstehung eines fruchtbaren Bastardes (haploid $4n^2$) aus der Kreuzung von *Ch. marginatum* (hapl. 5n) mit *Ch. morifolium* (hapl. 3n), Journal of Science of the Hiroshima University, Series B, Div. 2, vol. 1, Art. 8, 1932.

Ernest L. Scott, The Breeder's Handbook, 1957, pp. 1–76 Handbook No. 4, National Chrysanthemum Society, Inc., USA.

John Woolman, Chrysanthemums for Garden and Exhibition, 1953, pp. 1–103, W.H. & L. Collingridge Ltd., Tavistock Street, London WC2 and Transatlantic Arts Incorporated, Forest Hills, New York.

H.G. Witham Fogg, Chrysanthemum Growing, 1962, pp. 171, John Gifford Limited, London, W.C.2.

National Agricultural Statistics Service, USDA Additional Floriculture Information, pp. 1–84, National Agricultural Statistics Service, Floriculture Crops, 1998 Summary, Jun. 1999.

Handbook on Chrysanthemum Classification, A Publication of the Classification Committee National Chrysanthemum Society, Inc., U.S.A., 1996 Edition.

C. Ackerson, Chapter 12, Development of the Chrysanthemum in China, pp. 146–155, National Chrysanthemum Society Bulletin 1967.

C. Ackerson, Chapter 11, Original Species of the Chrysanthemum, pp. 105–107, National Chrysanthemum Society Bulletin, 1967.

G.J. Dowrick, The Chromosomes of Chrysanthemum I: The Species, *Heredity*, 6:365–375 (1952).

Junyu, C., et al., *Acta Horticulturae*, 404:30–36 (1995).

* cited by examiner

*Primary Examiner*—Anne Marie Grunberg

(74) *Attorney, Agent, or Firm*—Wood, Phillips, Katz, Clark & Mortimer

(57) ABSTRACT

A new and distinct Chrysanthemum plant named MN98-89-7 is provided. This new cultivar was the result of a cross between *Dendranthema weyrichii* and *Dendranthema× grandiflora*.

5 Drawing Sheets

Latin name of the genus and species of the plant claimed: Dendranthema×hybrida.

Variety denomination: 'MN98-89-7'.

BACKGROUND OF THE INVENTION

The present invention comprises a new and distinctive chrysanthemum plant, hereinafter referred to by the cultivarname 'MN98-89-7'. This new cultivar was the result of a cross in 1989 between *Dendrathema weyrichii* and *Chrysanthemum morifolim*. More specifically, the breeding program which resulted in the production of the new cultivar was carried out at St. Paul, Minn. The female or seed parent of MN98-89-7 was *Dendranthema weyrichii* 'Pink Bomb', commercially available from White Flower Farms, Connecticut having the following characteristics: (a) the plant habit is prostrate and the plant spreads via rhizomes to form a large mat after the first year; (b) the plant dimensions are that the plant has a diameter of about 1.5' and is about 5–6" tall; (c) the plant is hardy in zones 4–9 (Southeast)/Zone 10 (west); (d) the flower of the plant is a single daisy, having light lavender-colored ray florets and central disc florets with yellow pollen; (e) the plant has leaves that are dark green in color, with a very shiny leaf surface (glossy), and glabrous leaf margins that are deeply incised; and (f) the plant tends to rosette, needs cold treatment to flower consistently, flowering can be sporadic with gaps in the plant architecture and the plant is an obligate short-day plant. The male or pollen parent of 'MN98-89-7 ' was a *Dendranthema×grandiflora* which is commercially available from Yoder Brothers, Inc., Barberton, Ohio having the following characteristics: (a) the plant habit is cushion; (b) the plant dimensions are that the plant is similar to other cusion types commercially available from Yoder Brothers, Inc., such as, but not limited to the variety, 'Soft Cherie'; (c) the plant is hardy in zones 6–9 (Southeast)/Zone 10 (west); (d) the flower is a single or duplex daisy, possibly orange or bronze ray florets, central disc florets with yellow pollen; (e) the plant has leaves that are similar to other Yoder Brothers, Inc. cushion series chrysanthemums; and (f) the plant is a facultative short-day plant. The resulting seed, identified as '90-287-326' was collected. In 1991, a plant of '90-287-326' was crossed as the male parent with plants identified as '89-409-19', a University of Minnesota inbred parental selection, as the female parent and the resulting seeds, identified as cross number '92-321-19', collected. In 1997, plants of '92-321-19 ' were open-pollinated and the resulting seeds, identified as '98-87', collected and planted. The seventh (7) plant regenerated from said seed was identified as '98-87-7'.

Asexual reproduction of the new cultivar by terminal or stem cuttings taken during 1993 through 2000 at St. Paul, Minn. U.S.A. has demonstrated that the characteristics of the new cultivar as herein described are firmly fixed and are retained through successive generations of such asexual propagation.

SUMMARY OF THE INVENTION

It was found that the cultivar of the present invention:

(a) exhibits extreme hybrid vigor, (b) develops, in its second and subsequent years after planting, when grown in the fall under natural day-length and without the application of growth regulators, into a flowering herbaceous shrub having a plant height of from about 2.0 to about 3.0 feet and a spread from about 2.5 to about 5.0 feet, (c) exhibits, in its second and subsequent years after planting and during the fall season (August–October), a massive floral display, (d) displays flowers which are slightly toned with grey, giving the flower petals a slightly altered coloration, (e) exhibits superior winter hardiness, including frost tolerance, and (f) exhibits self-pinching.

The 'MN98-89-7' cultivar has not been observed under all possible environmental conditions to date. Accordingly, it is possible that the phenotype may vary somewhat with variations in the environment, such as temperature, light intensity, and day length.

When the new cultivar of the present invention is compared to 'Emily' (U.S. Plant Pat. No. 7,754), it is found to exhibit a more spreading and prolific habit accompanied with a massive floral display in its second and subsequent years after planting. Reference is made to Table A below which compares certain characteristics of 'MN98-89-7' to 'Emily'.

TABLE A

| CHARACTERISTIC | 'MN98-89-7' | 'Emily' |
|---|---|---|
| Plant Shape | cushion (mounded, spherical) | cushion |
| Plant height (1st year) | 1.5' | 1'–1.5' |
| (2nd year) | 2.0–3.0' | -(dead) |
| Flowering Response # weeks short days (SD) | 6.5 | 6.0 |
| Flower Type | Duplex daisy | Decorative |
| Flower Diameter | 5.0 cm | 4.5–5.0 cm |
| Ray florets, color, mature | | |
| Adaxial surface | RHS Red Purple Group 70A | RHS Red Purple Group 69D |
| Abaxial surface | RHS Red Purple Group 69D, 70D | RHS Red Purple Group 69A |

BRIEF DESCRIPTION OF THE PHOTOGRAPHS

The accompanying photographs show as nearly true as it is reasonably possible to make the same in color illustrations of this type, typical flower and foliage characteristics of the new cultivar. The plants were grown in a greenhouse at St. Paul, Minn., USA.

DETAILED BOTANICAL DESCRIPTION

Figure 1:
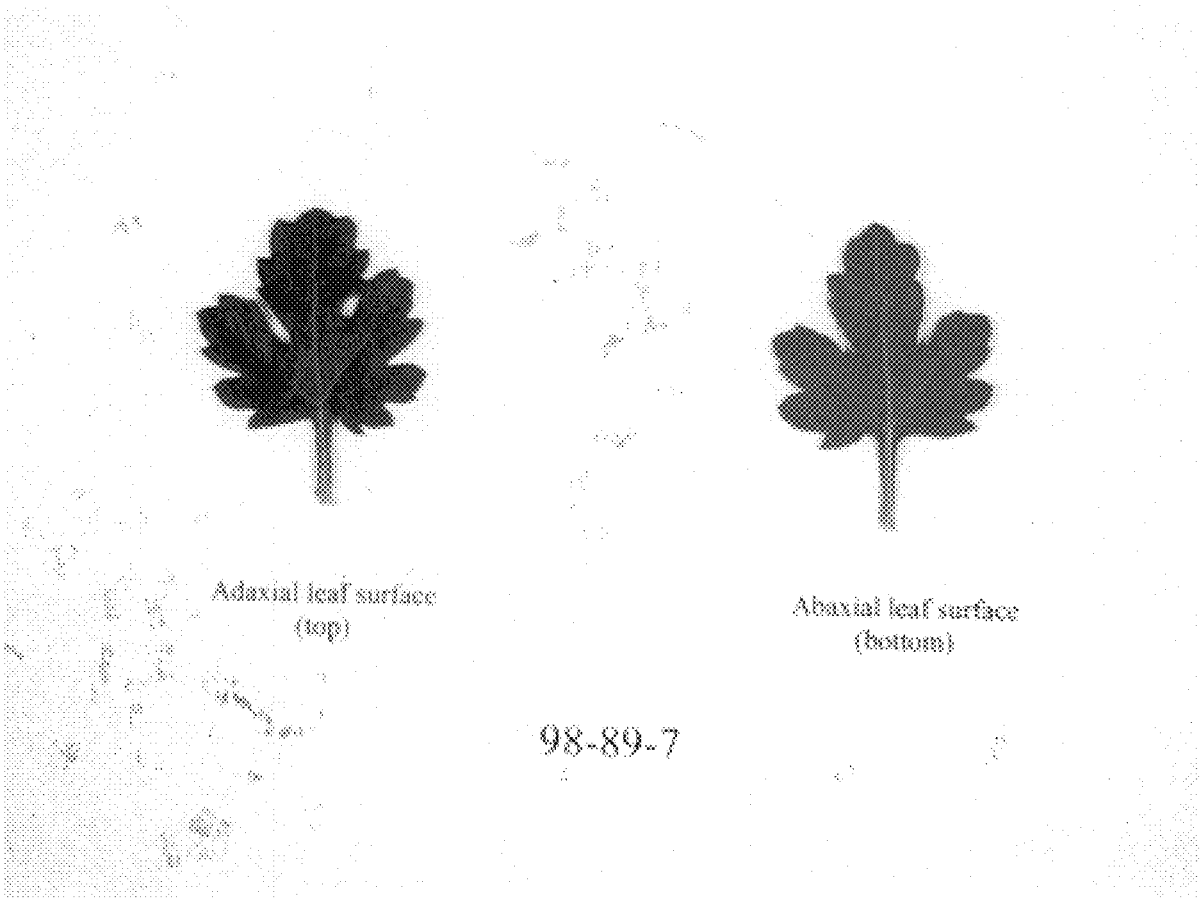
FIG. 1 shows an adaxial and abaxial views of the leaf shape of chrysanthemum variety 'MN98-89-7'.
Figure 2:
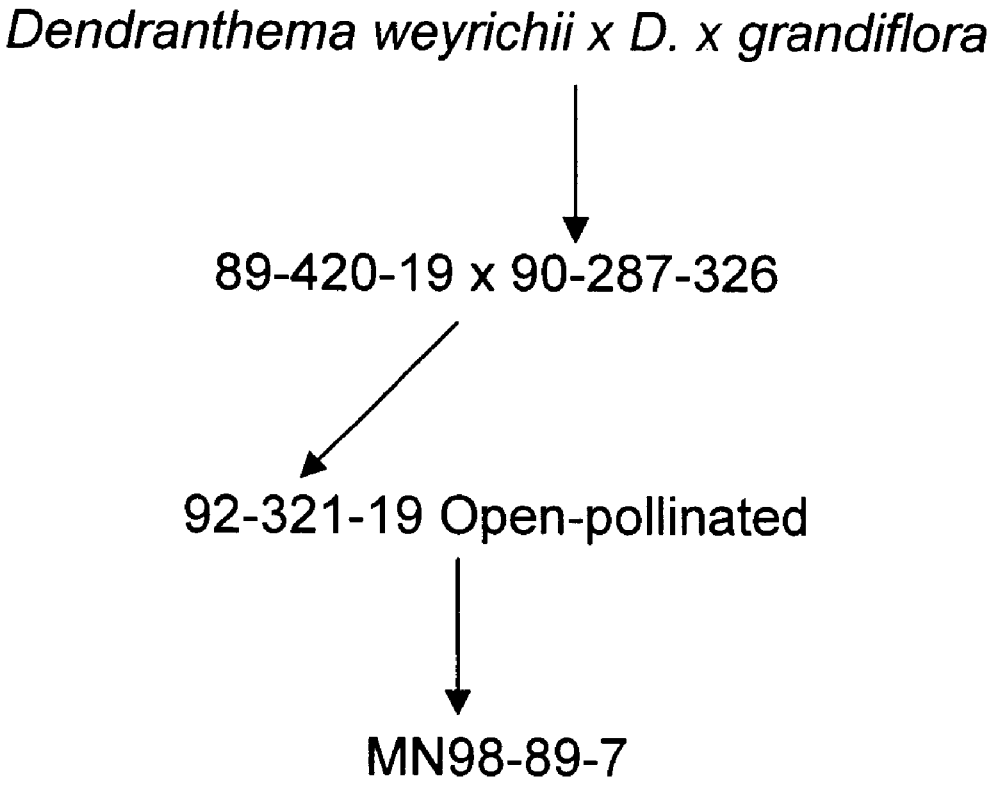
FIG. 2 shows the breeding history of chrysanthemum variety 'MN98-89-7'.
Figure 3:
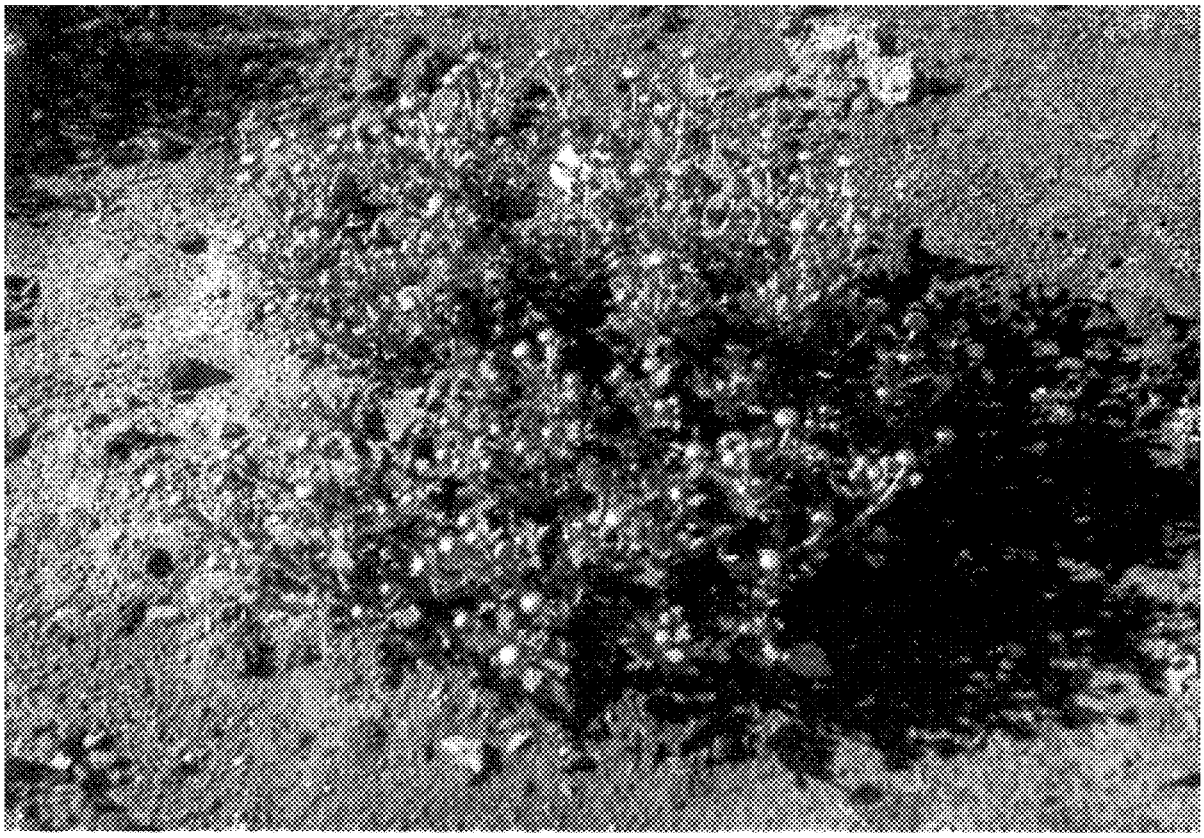
FIG. 3 is a color photograph of chrysanthemum variety 'MN98-89-7' after one year of growth.
Figure 4:
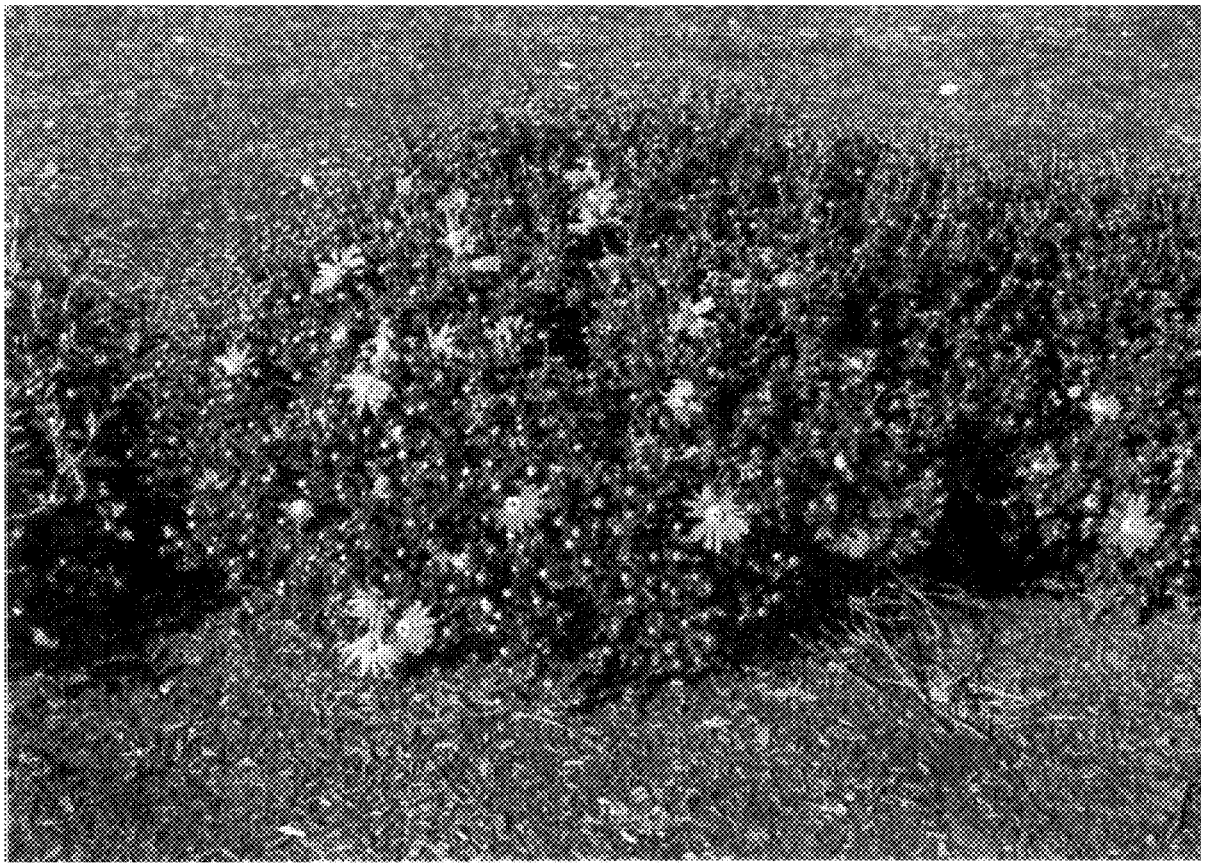
FIG. 4 is a color photograph of chrysanthemum variety 'MN98-89-7' after two years of growth.
Figure 5:
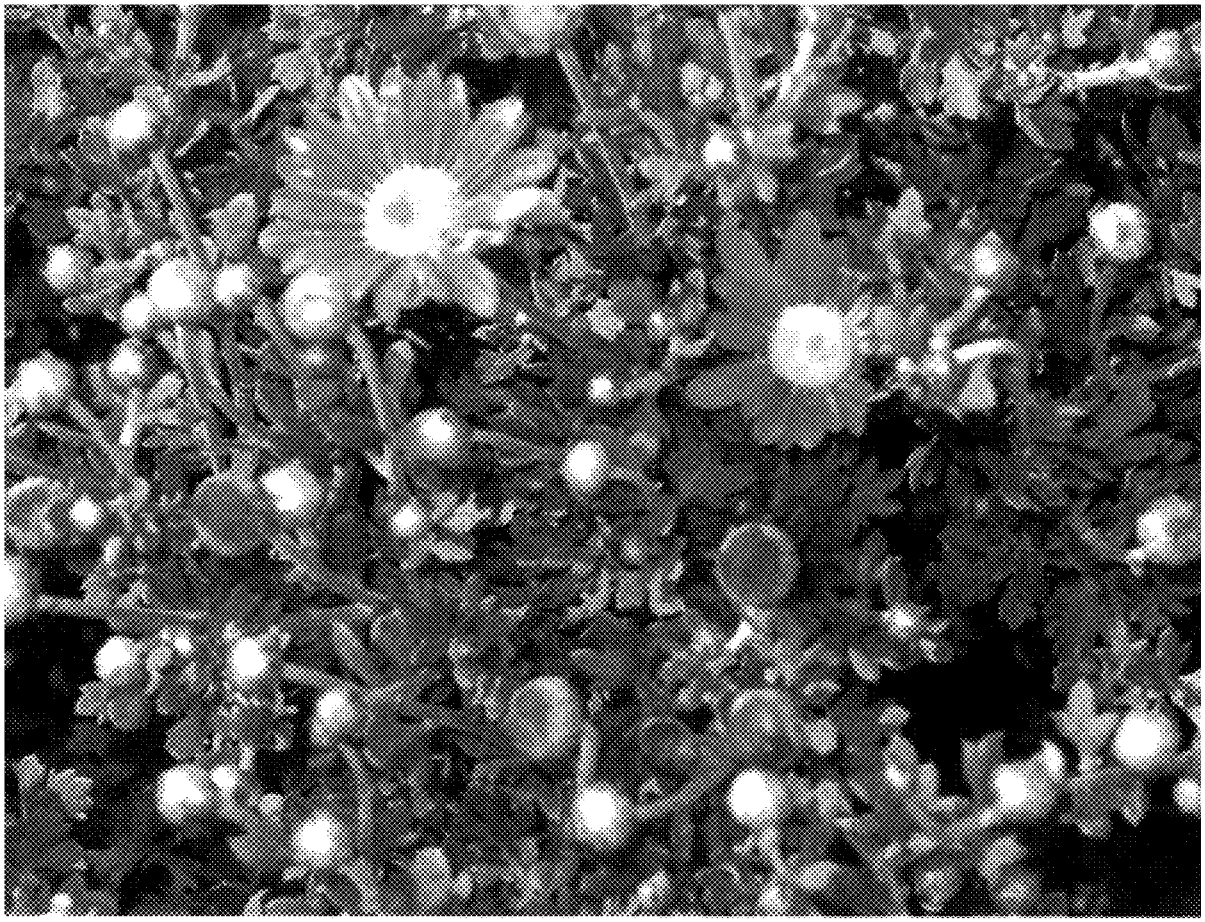
FIG. 5 is a color photograph of chrysanthemum variety 'MN98-89-7' showing a close-up of the bloom.

The chart used in the identification of colors described herein is The R.H.S. Colour Chart of The Royal Horticultural Society, London, England (1995 Edition). The color values were determined on Jan. 18, 2001 in St. Paul, Minn. The readings were taken between 1:00 and 3:00 p.m. under approximately 2500 footcandles of light. The plants were produced from cuttings taken from stock plants and were grown under greenhouse conditions comparable to those used in commercial practice while utilizing a soilless growth medium and maintaining temperatures of approximately 72° F. during the day and approximately 65° F. during the night.

Propagation:

*Type.*—Herbaceous stem cutting.

*Time to rooting.*—About 1 week.

*Rooting habit.*—Vigorous.

Plant description:

*Appearance, shape.*—Mounded spherical (first year). Mounded spherical (Second year).

*Appearance, growth habit.*—Mound.

*Appearance, growth rate/vigor.*—Vigorous.

*Plant height.*—about 15 inches (first year). About 2 to 3 feet (second year) (estimated).
*Lateral branch length.*—About 6–11 inches.
*Quantity of lateral branches after removal of apical meristem.*—One per node.
*Stem color.*—RHS Yellow Green Group 148B.

Foliage description:
*Number of leaves per plant.*—Greater than 3,000 (Second year).
*Number of leaves per lateral branch.*—5 to 20.
*Leaf arrangement.*—Alternate.
*Leaf size, fully expanded, length.*—7.2 cm.
*Leaf size, fully expanded, width.*—5.3 cm.
*Leaf apex.*—Rounded at tips; truncate side edges.
*Leaf base.*—Truncate.
*Leaf margin.*—Incised (Mulberry-like incisions).
*Leaf texture.*—Glaucous.
*Petiole length.*—2.7 cm.
*Color, young foliage adaxial surface.*—RHS Green Group 137A.
*Color, young foliage abaxial surface.*—RHS Yellow Green Group 148B.
*Color, fully expanded foliage adaxial surface.*—RHS Green Group 139A.
*Color, fully expanded foliage abaxial surface.*—RHS Yellow Green Group 147B.
*Color, venation adaxial surface.*—RHS Yellow Green Group 147C.
*Color, venation abaxial surface.*—RHS Yellow Green Group 147B.
*Color, petiole.*—RHS Yellow Green Group 148C.

Phyllary description:
*Appearance.*—The involucral bracts (phyllaries) are crenulate with entire margins.
*Color.*—RHS Green Group 138C.
*Texture.*—Glabrous.
*Size.*—Approximately 0.2–0.4 cm in length.

Inflorescence description:
*Appearance.*—Head (composite), duplex daisy.
*Flowering response.*—About 6.5 weeks (SD).
*Quantity of inflorescences.*—Greater than 3,000 (Second year). About 500 (First year).
*Inflorescence size, diameter.*—5.2 cm.
*Inflorescence size, depth (height).*—0.8 cm.
*Inflorescence size, diameter of disc.*—1.4 cm.
*Opening inflorescences, bud shape.*—Conical, upright.
*Opening inflorescences, bud size, length.*—1.9 cm.
*Opening inflorescences, bud size, width.*—1.0 cm.
*Opening inflorescences. bud color.*—RHS Red Purple Group 59A.
*Ray florets, shape.*—Spatulate.
*Ray florets, size, length.*—2.45 cm.
*Ray florets, size, width.*—0.54 cm.
*Ray florets, apex.*—Rounded.
*Ray florets, base.*—Cuneate.
*Ray florets, margin.*—Entire.
*Ray florets, texture.*—Glabrous.
*Ray florets, aspect.*—Horizontal to slightly recurved down.
*Number of ray florets per inflorescence.*—About 25.
*Ray florets, color, when opening, adaxial surface.*—RHS Red-Purple Group 71A.
*Ray florets, color, when opening, abaxial surface.*—RHS Red Purple Group 71C & Red Purple Group 69C.
*Ray florets, color, mature adaxial surface.*—RHS Red Purple Group 70A.
*Ray florets, color, mature, abaxial surface.*—RHS Red Purple Group 69D & 70D.
*Ray florets, color, fading to.*—RHS Red Purple Group 70C.
*Disc florets, shape.*—Tubular, rounded at tip.
*Disc florets, size, length.*—0.6 cm.
*Disc florets, size, width.*—0.1 cm.
*Number of disc florets per inflorescence.*—About 144.
*Disc florets, color, immature.*—RHS Yellow Green Group 150A. Disc florets, color, mature RHS Yellow Group 3A.
*Peduncle, aspect, strength.*—Stiff.
*Peduncle, aspect, angle to stem.*—45°.
*Peduncle, length, first peduncle.*—3.0 cm.
*Peduncle, length, fourth peduncle.*—2.0 cm.
*Peduncle, texture.*—Hirsute.
*Peduncle, color.*—RHS Green Group 138B.
*Reproductive organs, androecium, floret location.*—Disc florets.
*Anther color.*—RHS Yellow Group 5A.
*Pollen, abundance.*—Abundant.
*Pollen, color.*—RHS Yellow Group 4A.
*Reproductive organs, gynoecium, floret location.*—Disc/ray florets.
*Style color.*—RHS Yellow Group 6C.
*Disease resistance.*—'MN98-89-7' has not been tested for any disease susceptibility, tolerance or resistance.
*Seed production and fruit.*—About 169 ovules/flower. The fruit is an achene, a dry, indehiscent fruit with a single locule and a single seed, and with the seed attached to the ovary wall at a single point. The achene does not have any pappus of awns or bristles; its general shape is a half-inflated football oval with pointed ends. Seed Size is about 0.2–0.5 cm in length and about 0.1–0.2 cm in width. The surface texture is ridged. The color designation for the seed is RHS Brown Group 200D.
*Winter Hardiness.*—Hardy in zones 3–10 in uncovered field conditions without the need for added protection such as snow fences, mulch, etc.
*Frost tolerance.*—Yes, extends blooming season to the first freeze in the north (In zones 3–4 the first frost usually takes place between September 1–15. In zones 3–4, the first freeze usually takes place between October 1–20).
*Fragrance.*—Fragrance is noticeable when handling or bruising the foliage.
*Longevity of the bloom.*—Flower longevity is temperature dependent. Under normal conditions in the field, during the fall season, flowers will typically last about 2–4 plus weeks.
*Is the plant rhizomatous?.*—Yes.

What is claimed is:

1. A new and distinct chrysanthemum plant as herein described and illustrated.

* * * * *